(12) United States Patent
Marcus

(10) Patent No.: US 11,648,235 B1
(45) Date of Patent: May 16, 2023

(54) TREATMENT OF GLIOBLASTOMA

(71) Applicant: Cantex Pharmaceuticals, Inc., Weston, FL (US)

(72) Inventor: Stephen G. Marcus, Weston, FL (US)

(73) Assignee: Cantex Pharmaceuticals, Inc., Weston, FL (US)

(*) Notice: Subject to any disclaimer, the term of this patent is extended or adjusted under 35 U.S.C. 154(b) by 0 days.

(21) Appl. No.: 18/148,922

(22) Filed: Dec. 30, 2022

(51) Int. Cl.
  *A61K 31/4164* (2006.01)
  *A61K 31/495* (2006.01)
  *A61N 5/10* (2006.01)
  *A61P 25/00* (2006.01)
  *A61P 35/00* (2006.01)

(52) U.S. Cl.
  CPC ........ *A61K 31/4164* (2013.01); *A61K 31/495* (2013.01); *A61N 5/10* (2013.01); *A61P 25/00* (2018.01); *A61P 35/00* (2018.01)

(58) Field of Classification Search
  CPC .... A61K 31/4164; A61K 31/495; A61N 5/10; A61P 25/00; A61P 35/00
  See application file for complete search history.

(56) References Cited

U.S. PATENT DOCUMENTS

| 7,361,678 | B2* | 4/2008 | Mjalli | C07D 401/06 514/397 |
|---|---|---|---|---|
| 7,884,219 | B2 | 2/2011 | Hari | |
| 8,372,988 | B2 | 2/2013 | Hari | |
| 9,717,710 | B2 | 8/2017 | Orlandi et al. | |
| 10,363,241 | B2 | 7/2019 | Valcarce | |
| 11,524,942 | B2 | 12/2022 | Banner et al. | |
| 2021/0059988 | A1 | 3/2021 | Hu | |
| 2021/0070714 | A1 | 3/2021 | Wu | |
| 2021/0338639 | A1 | 11/2021 | Jones et al. | |

FOREIGN PATENT DOCUMENTS

WO  WO 2019/094613 A1  5/2019

OTHER PUBLICATIONS

Alban, TJ, et al., "Global immune fingerprinting in glioblastoma patient peripheral blood reveals immune-suppression signatures associated with prognosis," *JCI Insight*, Nov. 2, 2018;3(21):e122264, pp. 1-15.
Al-Kharboosh, R., et al., "Inflammatory Mediators in Glioma Microenvironment Play a Dual Role in Gliomagenesis and Mesenchymal Stem Cell Homing: Implication for Cellular Therapy," Mayo Clin Proc Innov Qual Outcomes. Aug. 5, 2020;4(4):443-459.
Allette, Y.M., et al., Author manuscript, "Identification of functional interaction of HMGB1 with receptor for advanced glycation end-products in a model of neuropathic pain," *Brain, Behavior, and Immunity*, vol. 42, Nov. 2014, pp. 169-177.
Alnahhas, I., et al., "Characterizing benefit from temozolomide in MGMT promoter unmethylated and methylated glioblastoma: a systematic review and meta-analysis" with Erratum, *Neuro-Oncology Advances*, Oct. 2020, vol. 2, Issue 1, 8 pages.
Angelopoulou, E., et al. "Pivotal role of high-mobility group box 1 (HMGB1) signaling pathways in glioma development and progression," *Journal of Molecular Medicine*, Aug. 2016;94(8):867-74. doi: 10.1007/s00109-016-1435-y.
Bassi, R., et al., "HMGB1 as an autocrine stimulus in human T98G glioblastoma cells: role in cell growth and migration," *Journal of Neuro-Oncology*, Mar. 2008, 87(1):23-33.
Batchelor, T., "Patient education: High-grade glioma in adults (Beyond the Basics)," Wolters Kluwer, 2022, 11 pages.
Chen, X., et al., "RAGE expression in tumor-associated macrophages promotes angiogenesis in glioma," *Cancer Research*, Dec. 15, 2014;74(24):7285-7297.
ClinicalTrials.gov, NTC05635735: Azeliragon and Chemoradiotherapy in Newly Diagnosed Glioblastoma, Information provided by Cantex Pharmaceuticals, Dec. 2, 2022, 10 pages.
Demers, M., et al., "Neutrophil extracellular traps: A new link to cancer-associated thrombosis and potential implications for tumor progression," *Oncoimmunology*, vol. 2, Issue 2, Feb. 2013, article e22946, pp. 1-3.
Dyhrfort, P., et al., "Monitoring of protein biomarkers of inflammation in human traumatic brain injury using microdialysis and proximity extension assay technology in neurointensive care," *Journal of Neurotrauma*, 2019; 36:2872-85.
El-Far, A.H., et al., "Role and Mechanisms of RAGE-Ligand Complexes and RAGE-Inhibitors in Cancer Progression," *International Journal of Molecular Sciences*, vol. 21, Issue 10, 2020, Article 3613, pp. 1-21.
Gao, H., et al., "S100B suppression alters polarization of infiltrating myeloid-derived cells in gliomas and inhibits tumor growth," *Cancer Letters*, Dec. 28, 2018; 439:91-100.
Gao, TL, et al., "Expression of HMGB1 and RAGE in rat and human brains after traumatic brain injury," *The Journal of Trauma and Acute Care Surgery*, Mar. 2012, vol. 72, No. 3, pp. 643-649.
Gao, XY, et al., "Temozolomide Treatment Induces HMGB1 to Promote the Formation of Glioma Stem Cells via the TLR2/NEAT1/Wnt Pathway in Glioblastoma," *Frontiers in Cell and Developmental Biology*, Feb. 1, 2021; 9:620883, pp. 1-14.
Gilbert, MR, et al., "A randomized trial of bevacizumab for newly diagnosed glioblastoma," *The New England Journal of Medicine*, Feb. 20, 2014, 370(8):699-708.
Gilbert, MR, et al., "Dose-dense temozolomide for newly diagnosed glioblastoma: a randomized phase III clinical trial," *Journal of Clinical Oncology*, vol. 31, No. 32, Nov. 2013, pp. 4085-4091.
Hegi, ME, et al., "MGMT gene silencing and benefit from temozolomide in glioblastoma," The New England Journal of Medicine, Mar. 2005, vol. 352, No. 10, pp. 997-1003.

(Continued)

*Primary Examiner* — Erich A Leeser
(74) *Attorney, Agent, or Firm* — Fenwick & West LLP

(57) ABSTRACT

Methods of treating glioblastoma are provided comprising: administering a therapeutically effective amount of azeliragon, or a pharmaceutically acceptable salt thereof, and co-administering an effective amount of radiation therapy (RT), to a patient who has been diagnosed with glioblastoma. In another aspect, methods are provided for treating grade I, grade II, and grade III gliomas, the method comprising administering a therapeutically effective amount of azeliragon, or a pharmaceutically acceptable salt thereof, and co-administering an effective amount of radiation therapy (RT), to a patient who has been diagnosed with glioma.

30 Claims, 3 Drawing Sheets

(56) References Cited

OTHER PUBLICATIONS

Figure 1:
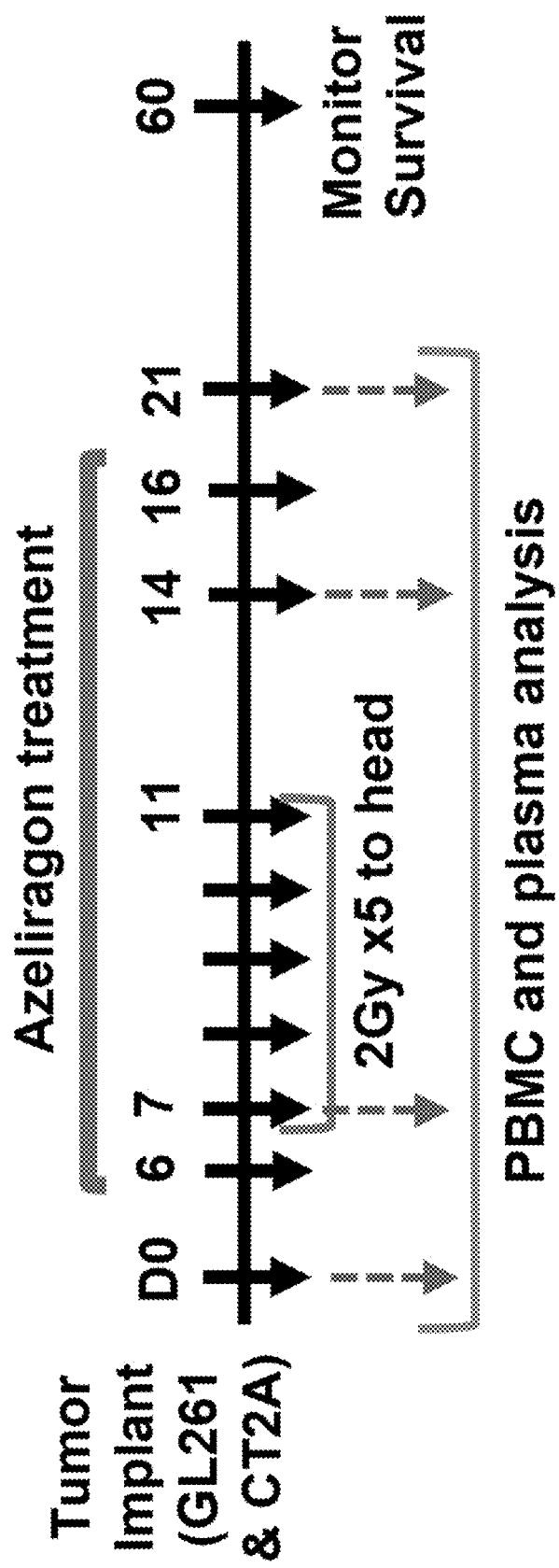

Hu, B., et al., "Identification of three glioblastoma subtypes and a six-gene prognostic risk index based on the expression of growth factors and cytokines" with Supplementary Materials, *American Journal of Translational Research*, vol. 12, Issue 8, pp. 4669-4682.

Kang, R., et al., "The receptor for advanced glycation end products (RAGE) sustains autophagy and limits apoptosis, promoting pancreatic tumor cell survival," *Cell Death and Differentiation*, Apr. 2010, 17(4):666-76.

Kim, HJ, et al., "Molecular Characteristics of RAGE and Advances in Small-Molecule Inhibitors," *International Journal of Molecular Sciences*, vol. 22, Issue 13, 2021, Article 6904, pp. 1-22.

Li, H., et al., "Inhibition of the receptor for advanced glycation end-products (RAGE) attenuates neuroinflammation while sensitizing cortical neurons towards death in experimental subarachnoid hemorrhage," *Molecular Neurobiology*, 2017; 54:755-67.

Li, R., "IL-6 augments the invasiveness of U87MG human glioblastoma multiforme cells via upregulation of MMP-2 and fascin-1," *Oncology Reports*, 2010; 23(6):1553-9. doi: 10.3892/or_00000795.

Liu, S., et al., "RAGE Inhibitors as Alternatives to Dexamethasone for Managing Cerebral Edema Following Brain Tumor Surgery," *Neurotherapeutics*, 2022, 19:635-648.

Monteiro, C., et al., "Stratification of radiosensitive brain metastases based on an actionable S100A9/RAGE resistance mechanism" with extended data and reporting summary, *Nature Medicine*, vol. 28, Apr. 2022, pp. 752-765.

Oh, T., et al., "Immunocompetent murine models for the study of glioblastoma immunotherapy," *Journal of Translational Research*, 2014, vol. 12, Article 107, pp. 1-10.

Okuma, Y, et al., "Glycyrrhizin inhibits traumatic brain injury by reducing HMGB1-RAGE interaction," *Neuropharmacology*, Oct. 2014; 85:18-26.

Ostrom, QT, et al., "CBTRUS Statistical Report: Primary Brain and Other Central Nervous System Tumors Diagnosed in the United States in 2011-2015" with Corrigendum, Neuro-Oncology, vol. 20, Issue Supplement 4, Oct. 2018, 101 pages.

Otazu, G.K., et al., "Role of RAGE and Its Ligands on Inflammatory Responses to Brain Tumors," *Frontiers in Cellular Neuroscience*, Dec. 2021, vol. 15, Article 770472, pp. 1-10.

Qiu, J., et al., "Early release of HMGB-1 from neurons after the onset of brain ischemia," *Journal of Cerebral Blood Flow & Metabolism*, 2008; 28:927-38.

Raychaudhuri, B., et al., "Myeloid-derived suppressor cell accumulation and function in patients with newly diagnosed glioblastoma," *Neuro-Oncology*, Jun. 2011;13(6):591-9.

Sarkaria, JN, et al., "Combination of temsirolimus (CCI-779) with chemoradiation in newly diagnosed glioblastoma multiforme (GBM) (NCCTG trial N027D) is associated with increased infectious risks," Clinical Cancer Research, Nov. 15, 2010;16(22):5573-80.

Stupp, R, et al., "Radiotherapy plus concomitant and adjuvant temozolomide for glioblastoma," *The New England Journal of Medicine*, Mar. 2005, vol. 352, No. 10, pp. 987-996.

Tafani, M., et al., "Pro-inflammatory gene expression in solid glioblastoma microenvironment and in hypoxic stem cells from human glioblastoma," Journal of Neuroinflammation, Apr. 13, 2011, vol. 8, Article 32, pp. 1-16, doi: 10.1186/1742-2094-8-32.

Vernon, PJ, et al., "The receptor for advanced glycation end products promotes pancreatic carcinogenesis and accumulation of myeloid-derived suppressor cells," *The Journal of Immunology*, Feb. 1, 2013;190(3):1372-9. doi: 10.4049/jimmunol.1201151.

Wang, D., et al., "Anti-high mobility group box-1 (HMGB1) antibody inhibits hemorrhage-induced brain injury and improved neurological deficits in rats," *Scientific Reports*, 2017, 7, Article No. 46243, pp. 1-16.

Wang, H., et al., "S100B promotes glioma growth through chemoattraction of myeloid-derived macrophages," *Clinical Cancer Research*, Jul. 15, 2013;19(14):3764-75.

Wen, PY, et al., "Updated response assessment criteria for high-grade gliomas: response assessment in neuro-oncology working group," *Journal of Clinical Oncology*, Apr. 10, 2010, 28(11):1963-72.

Wick, W., et al., "Phase II Study of Radiotherapy and Temsirolimus versus Radiochemotherapy with Temozolomide in Patients with Newly Diagnosed Glioblastoma without MGMT Promoter Hypermethylation (EORTC 26082)," *Clinical Cancer Research*, Oct. 1, 2016;22(19):4797-4806.

Zhang, J., et al., "Anti-high mobility group box-1 monoclonal antibody protects the blood-brain barrier from ischemia-induced disruption in rats," *Stroke*, 2011; 42:1420-8.

Zhang, P., et al., "Current Opinion on Molecular Characterization for GBM Classification in Guiding Clinical Diagnosis, Prognosis, and Therapy," *Frontiers in Molecular Biosciences*, Sep. 2020, vol. 7, Article 562798, pp. 1-12.

* cited by examiner

TREATMENT OF GLIOBLASTOMA

1. BACKGROUND OF THE INVENTION

Glioblastoma (GBM), which is a grade IV glioma, is the most common malignant primary brain tumor and one of the most devastating of all cancers. Between 2011 and 2015, there were 57,805 patients with newly-diagnosed GBM in the United States, for an annual average of 11,561 case per year. The current standard of care for GBM includes maximal safe surgical resection followed by radiation therapy (RT) and concurrent temozolomide (TMZ), and then adjuvant TMZ for 6 months. This regimen, also referred as the Stupp regimen, has been widely accepted as a standard of care for patients with newly-diagnosed GBM since 2005. Median overall survival (OS) for this standard of care treatment, however, is dismal, just 14.6 months, with a 2-year overall survival of only 26%. There is an urgent need for improved therapies that can prolong survival of glioblastoma patients.

2. SUMMARY OF THE INVENTION

As described herein, experiments were performed to assess the survival benefit of adding azeliragon administration to radiation therapy in treatment of glioblastoma, as compared to radiation therapy alone, using immune-competent murine orthotopic glioblastoma multiforme (GBM) tumor models. Azeliragon is an orally bioavailable inhibitor of the receptor for advanced glycation endproducts (RAGE). Results using two different murine GBM cell lines that are routinely used to model GBM in human patients demonstrated a significant improvement in survival when azeliragon was added to RT, as compared to administration of RT alone and azeliragon alone.

Accordingly, in a first aspect, methods of treating glioblastoma are provided. The method comprises administering a therapeutically effective amount of azeliragon, or a pharmaceutically acceptable salt thereof, and co-administering an effective amount of radiation therapy (RT), to a patient who has been diagnosed with glioblastoma.

In another aspect, methods of treating grade I glioma, grade II glioma, and grade III glioma are provided. The method comprises administering a therapeutically effective amount of azeliragon, or a pharmaceutically acceptable salt thereof, and co-administering an effective amount of radiation therapy (RT), to a patient who has been diagnosed with glioma.

3. BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 schematizes the experimental protocol used in Example 1 to assess the survival benefit of adding azeliragon administration to radiation therapy in treatment of glioblastoma, as compared to azeliragon administration alone and to radiation therapy alone, in immune-competent murine orthotopic glioblastoma multiforme (GBM) tumor models.

Figure 2:
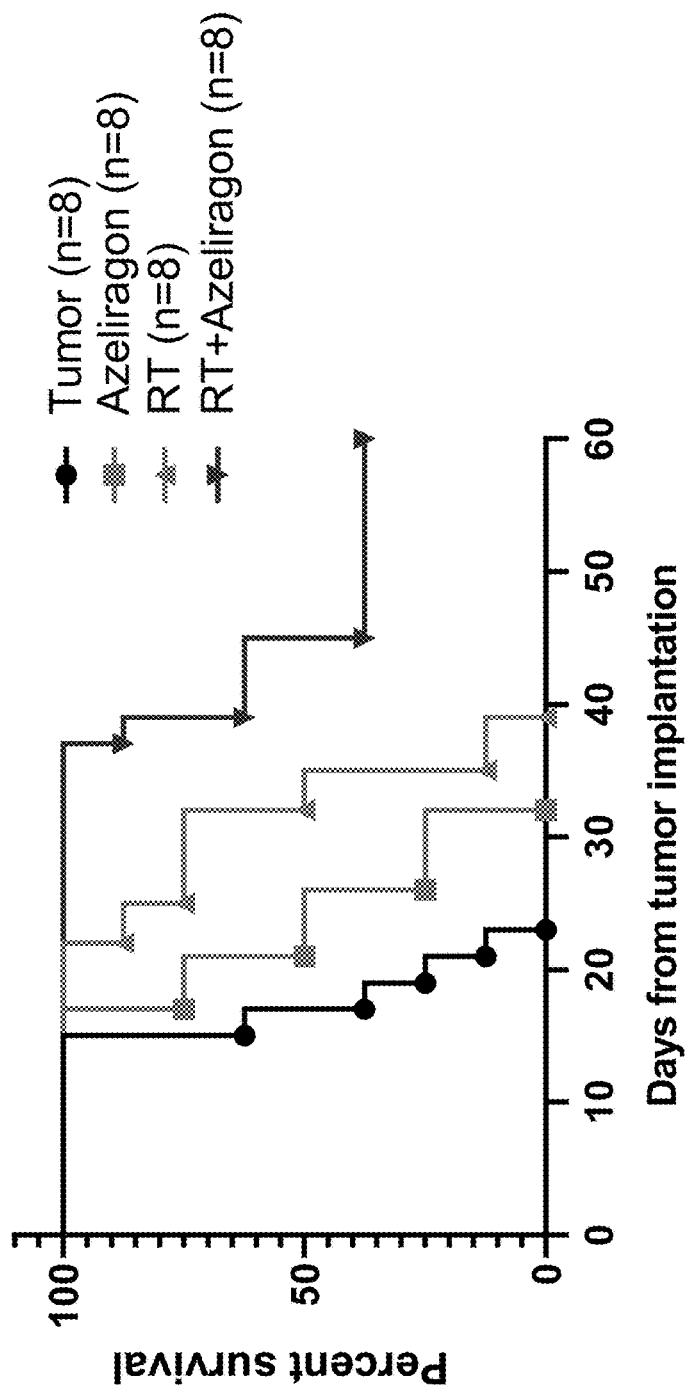

FIG. 2 presents Kaplan-Meier survival curves in four groups of C57 albino mice following GL261 cell implantation: control mice receiving no active treatment ("Tumor"), mice treated with azeliragon alone ("Azeliragon"), mice treated with radiation therapy alone ("RT"), and mice receiving both azeliragon and radiation therapy ("RT+Azeliragon"). The data show a significant improvement in survival with the combination therapy.

Figure 3:
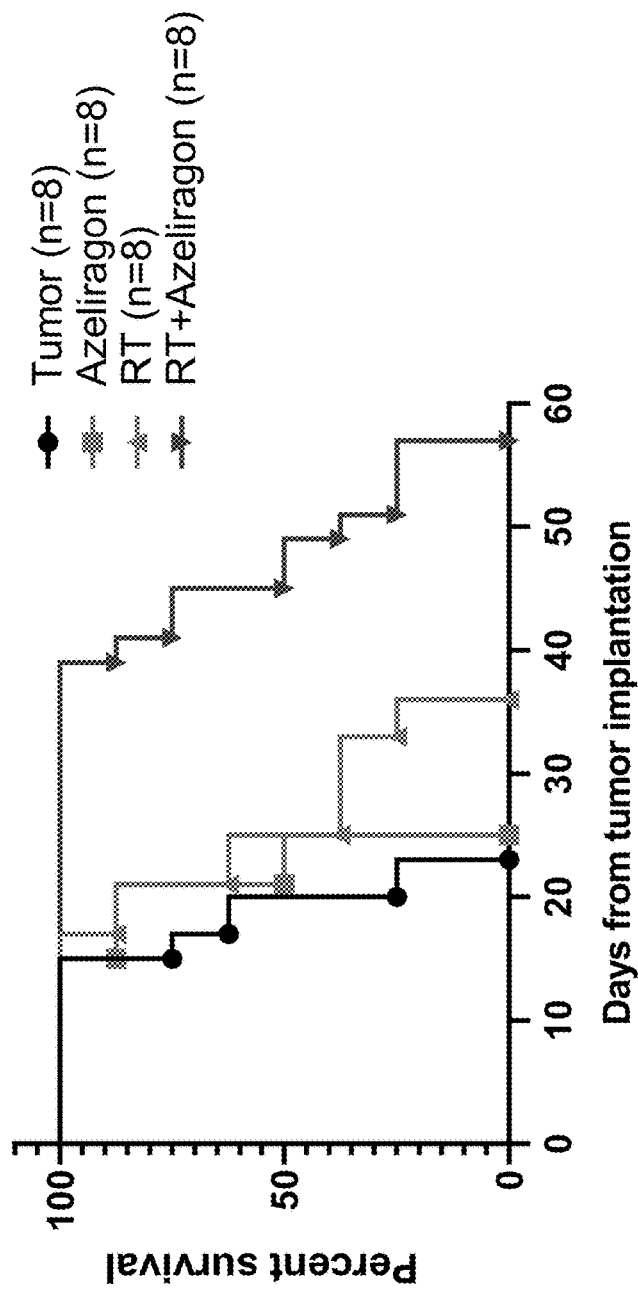

FIG. 3 presents Kaplan-Meier survival curves in four groups of C57 albino mice following CT2A cell implantation: control mice receiving no active treatment ("Tumor"), mice treated with azeliragon alone ("Azeliragon"), mice treated with radiation therapy alone ("RT"), and mice receiving both azeliragon and radiation therapy ("RT+Azeliragon"). The data show a significant improvement in survival with the combination therapy.

4. DETAILED DESCRIPTION OF THE INVENTION

4.1. Definitions

Unless otherwise defined herein, all technical and scientific terms used herein have the meaning commonly understood by one of ordinary skill in the art to which the invention pertains.

As used in this specification and the appended claims, the singular forms "a", "an", and "the" include plural references unless the context clearly dictates otherwise.

As used herein, the term "patient" refers to a human "subject."

The terms "treat", "treated", "treating", or "treatment" as used herein have the meanings commonly understood in the medical arts, and therefore do not require cure or complete remission, and therefore include any beneficial or desired clinical results. A "therapeutically effective amount" of a compound, composition, or radiation is an amount effective to treat.

The term "pharmaceutically acceptable salt" refers to salts derived from a variety of organic and inorganic counterions that are approvable by health regulators for inclusion in a drug substance. Suitable salts include those described in Stahl and Wermuth (Eds.), *Pharmaceutical Salts: Properties, Selection, and Use*, $2^{nd}$ revised edition, 2011.

The terms "co-administer" and "co-administering" refer to treatment regimens in which a plurality of different therapeutic compounds, or at least one therapeutic compound and radiation therapy (RT), are administered to a subject in sufficient temporal proximity to one another as to provide clinical benefit greater than administration of either, or any one, alone. Co-administration may involve separate simultaneous, or sequential, administration of a plurality of different therapeutic compounds, or of at least one therapeutic compound and radiation therapy (RT).

4.2. Methods of Treating Glioblastoma or Glioma

In a first aspect, methods of treating glioblastoma are presented. The method comprises administering a therapeutically effective amount of azeliragon, or pharmaceutically acceptable salt thereof, and co-administering an effective amount of radiation therapy (RT), to a patient who has been diagnosed with glioblastoma. The first aspect can alternatively be worded as azeliragon, or a pharmaceutically acceptable salt thereof, for use in a method of treating glioblastoma (GBM), comprising: administering a therapeutically effective amount of azeliragon, or a pharmaceutically acceptable salt thereof, and co-administering an effective amount of radiation therapy (RT), to a patient who has been diagnosed with glioblastoma.

4.2.1. Patient Selection

In typical embodiments, the patient has been diagnosed with glioblastoma (glioblastoma multiforme, GBM, WHO grade IV).

In certain embodiments, the patient has classical GBM. In certain embodiments, the patient has proneural GBM. In certain embodiments, the patient has neural GBM. In certain embodiments, the patient has mesenchymal GBM. In certain embodiments, the patient has gliosarcoma.

In some embodiments, the patient has primary GBM. In some embodiments, the patient has secondary GBM.

In various embodiments, cells within the patient's tumor have IDH (isocitrate dehydrogenase) mutations. In various embodiments, the patient's tumor is IDH-wildtype glioblastoma.

In some embodiments, the $O^{(6)}$-methylguanine DNA methyltransferase (MGMT) promoter in tumor cells is methylated. In some embodiments, the $O^{(6)}$-methylguanine DNA methyltransferase (MGMT) promoter in the tumor is unmethylated.

In some embodiments, cells in the tumor have a mutation in at least one gene selected from TP53, EGFR, PTEN, NF1 (Neurofibromin 1), PIK3CA (Phosphatidylinositol 4,5-bisphosphate 3-kinase catalytic subunit alpha isoform), PIK3R1 (Phosphatidylinositol 3-kinase regulatory subunit alpha), RB1 (Retinoblastoma-associated protein 1), SPTA1 (Spectrin alpha chain, erythrocytic 1), ATRX, IDH1, KEL, PDGFRA (Platelet-derived growth factor receptor A), and GABRA6 (Gamma-aminobutyric acid receptor subunit alpha-6).

In some embodiments, the patient is an adult. In various embodiments, the patient is at least 18 years old, 21 years old, 30 years old, 40 years old, 50 years old, 60 years old, 70 years old, 75 years old, or 80 years old.

In some embodiments, the patient is an infant or child. In various embodiments, the patient is no more than 1 year old, 2 years old, 3 years old, 4 years old, 5 years old, 6 years old, 7 years old, 8 years old, 9 years old or 10 years old. In various embodiments, the patient is no more than 15 years old, 16 years old, or 17 years old.

In another aspect, the patient has been diagnosed with grade I, grade II, or grade III glioma. In certain embodiments, the patient has a grade II or grade III astrocytic tumor. In certain embodiments, the patient has a grade II or grade III oligodendroglioma.

4.2.2. Azeliragon Drug Substance and Drug Product

"Azeliragon", also known as "TTP448" and "PF-04494700", CAS Registry No. 603148-36-3, is an orally bioavailable inhibitor of the receptor for advanced glycation endproducts (RAGE) having the structure of Formula I

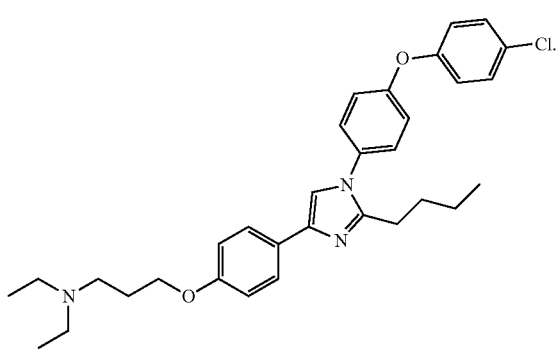

Formula I

Azeliragon's IUPAC chemical name is 3-[4-[2-butyl-1-[4-(4-chlorophenoxy)phenyl]imidazol-4-yl]phenoxy]-N,N-diethylpropan-1-amine. An alternative chemical name is N-[3-[4-[2-butyl-1-[4-(4-chlorophenoxy)phenyl]-1H-imidazol-4-yl]phenoxy]propyl]-N,N-diethylamine. U.S. Pat. Nos. 7,361,678, 7,884,219, and 8,372,988, the disclosures of which are hereby incorporated by reference in their entireties, describe azeliragon and methods of synthesizing azeliragon.

In some embodiments, azeliragon is administered in a crystalline form. In various embodiments, azeliragon is administered in a crystalline form described in any one of U.S. Pat. Nos. 7,884,219; 8,372,988; and US pre-grant publication No. US 2021/0070714, the disclosures of which are hereby incorporated by reference in their entireties.

In certain embodiments, azeliragon is administered as crystalline Form I, characterized as having a solid state $^{13}$C NMR spectrum comprising peaks at 149.7 and 141.0 ppm; having X-ray powder diffraction peaks expressed in degrees 2θ at 16.5° and 26.8°; and/or having a Raman spectrum comprising peaks at 335 and 798 $cm^{-1}$, as described in U.S. Pat. No. 7,884,219, herein incorporated by reference.

In certain embodiments, azeliragon is administered as crystalline Form II, characterized as having a solid state $^{13}$C NMR spectrum comprising peaks at 153.6, 140.1 and 119.9 ppm; having X-ray powder diffraction peaks expressed in degrees 2θ at 18.8° and 20.1° ; and/or having a Raman spectrum comprising peaks at 300 and 1180 $cm^{-1}$, as described in U.S. Pat. No. 7,884,219 and incorporated herein by reference.

In certain embodiments, azeliragon is administered as crystalline Form III, characterized as having an XRPD pattern comprising peaks at 2θ angles of 5.4°, 21.5°, and 22.0°±0.2°; and/oor an XRPD pattern characterized in FIG. 1 of US PreGrant publication 2021/0070714, incorporated herein by reference.

In some embodiments, azeliragon is administered as crystalline Form IV, characterized as having an XRPD pattern comprising peaks at 2θ angles of 19.7°, 22.0°, and 30.2°±0.2°, as described in US PreGrant publication 2021/0070714, incorporated herein by reference.

In some embodiments, azeliragon is amorphous.

In some embodiments, azeliragon is administered as the free base.

In some embodiments, azeliragon is administered in the form of a pharmaceutically acceptable salt. In various embodiments, the azeliragon salt is a salt described in US pre-grant publication No. 2021/0059988, the disclosure of which is incorporated herein by reference in its entirety. In particular embodiments, azeliragon is administered in the form of a pharmaceutically acceptable salt selected from the group consisting of 4-aminosalicylic acid, fumaric acid, galactaric acid, gentisic acid, hippuric acid, hydrobromic acid, hydrochloric acid, maleic acid, L-malic acid, methane sulfonic acid, oxalic acid, phosphoric acid, saccharin, L-tartaric acid, and vanillic acid.

In some embodiments, azeliragon is administered in a liquid formulation.

In some embodiments, azeliragon is administered in a solid dosage form, for example a solid oral dosage form. In particular embodiments, the solid dosage form is a tablet. In particular embodiments, the solid dosage form is a capsule.

4.2.3. Azeliragon Dose Regimen

In typical embodiments, azeliragon is administered orally. In various embodiments, azeliragon is administered without regard to food.

In some embodiments, azeliragon is administered daily for a first plurality of days at a loading dose, followed by daily administration thereafter for a second plurality of days at a maintenance dose.

In various embodiments, the loading dose is administered daily for at least 5 days, 6 days, 7 days, 8 days, 9 days, 10 days, 11 days, 12 days, 13 days, or 14 days. In various embodiments, the loading dose is administered daily for 5 days, 6 days, 7 days, 8 days, 9 days, 10 days, 11 days, 12 days, 13 days, or 14 days. In certain embodiments, the first loading dose is administered at least 5 days, 6 days, 7 days, 8 days, 9 days, 10 days, 11 days, 12 days, 13 days, or 14 days before commencing RT. In certain embodiments, the first loading dose is administered 5 days, 6 days, 7 days, 8 days, 9 days, 10 days, 11 days, 12 days, 13 days, or 14 days before commencing RT.

In certain embodiments, the first maintenance dose is administered before commencing RT. In certain embodiments, the first maintenance dose is administered on the same day that RT commences. In certain embodiments, the first maintenance dose follows commencement of RT. In some embodiments, azeliragon is administered at the maintenance dose daily for at least 3 months, 6 months, 9 months, or 12 months. In some embodiments, azeliragon is administered at the maintenance dose daily for 3 months, 6 months, 9 months, or 12 months. In some embodiments, azeliragon is administered at the maintenance dose daily for at least 15 months, 18 months, 21 months, or 24 months. In some embodiments, azeliragon is administered at the maintenance dose daily for 15 months, 18 months, 21 months, or 24 months. In some embodiments, azeliragon is administered at the maintenance dose daily for at least 3 years, 4 years, 5 years, 6 years, 7 years, 8 years, 9 years, or 10 years. In some embodiments, azeliragon is administered at the maintenance dose daily for 3 years, 4 years, 5 years, 6 years, 7 years, 8 years, 9 years, or 10 years. In some embodiments, azeliragon is administered at the maintenance dose for the rest of the patient's life.

In some embodiments, the loading dose is 60 mg per day, 30 mg per day or 15 mg per day. In some embodiments, the maintenance dose is 20 mg per day, 10 mg per day or 5 mg per day. The daily loading dose and/or daily maintenance dose can be administered as a single daily dose or as a plurality of split doses administered multiple times per day, such as twice per day or three times per day.

In certain embodiments, the loading dose is 30 mg twice daily (60 mg daily dose) and the maintenance dose is 20 mg once daily. In specific embodiments, the loading dose is 30 mg twice daily for 6 days and the maintenance dose is 20 mg once daily for at least 3 months, 6 months, 9months, or 12 months. In certain embodiments, the loading dose is 15 mg twice daily (30 mg daily dose) and the maintenance dose is 10 mg once daily. In specific embodiments, the loading dose is 15 mg twice daily for 6 days and the maintenance dose is 10 mg once daily for at least 3 months, 6 months, 9 months, or 12 months. In certain embodiments, the loading dose is 15 mg once daily and the maintenance dose is 5 mg once daily. In specific embodiments, the loading dose is 15 mg once daily for 6 days and the maintenance dose is 5 mg once daily for at least 3 months, 6 months, 9 months, or 12 months.

4.2.4. Radiation Therapy (RT)

In typical embodiments, radiation therapy is fractionated radiotherapy. In certain embodiments, RT is fractionated conformal radiotherapy. In certain embodiments, RT is fractionated focal irradiation. In certain embodiments, RT is intensity-modulated radiotherapy (IMRT). In certain embodiments, RT is image-guided radiation therapy. In certain embodiments, RT is stereotactic RT.

In certain embodiments, RT is administered at a daily dose of 2 gray (Gy). In certain embodiments, RT is administered at a daily dose of 2 Gy for 5 days a week for 6 weeks, for a total dose of 60 Gy.

In some conformal embodiments, RT is delivered to an initial volume consisting of the area of enhancement, the postoperative cavity, plus surrounding edema (or other abnormality as seen on fluid attenuated inversion recovery [FLAIR] images on MRI), and a 2-cm margin. In certain embodiments, the total dose is 46 Gy in 23 fractions, followed by a boost of 14 Gy in 7 fractions to the area of enhancement plus the cavity and a 2.5-cm margin.

In some embodiments, the RT is proton therapy.

In some embodiments, the RT dose is administered after azeliragon has been administered daily at the loading dose for 5 days, 6 days, 7 days, 8 days, 9 days, 10 days, 11 days, 12 days, 13 days, or 14 days. In some embodiments, the first RT dose is administered after azeliragon has been administered daily at the loading dose for 5 days, 6 days, 7 days, 8 days, 9 days, 10 days, 11 days, 12 days, 13 days, or 14 days and azeliragon has thereafter been administered daily at the maintenance dose for 1 day, 2 days, 3 days, 4 days, 5 days, 6 days, 7 days, 8 days, 9 days, 10 days, 11 days, 12 days, 13 days, or 14 days.

In preferred embodiments, the first RT dose is administered after azeliragon has been administered at the loading dose for 6 days or 7 days. In preferred embodiments, RT begins on the same day as the first administration of the azeliragon maintenance dose.

4.2.5. Prior Surgery

In typical embodiments, the patient's tumor has been surgically resected prior to initiation of administration of azeliragon and co-administration of RT.

4.2.6. Optional Chemotherapy

In some embodiments, the method optionally further comprises administering a chemotherapeutic agent.

In preferred embodiments, the chemotherapeutic agent is temozolomide (TMZ). In certain embodiments, temozolomide is administered orally at a daily dose of 75 mg per square meter of body surface. In certain embodiments, TMZ is administered orally at a daily dose of 75 mg/m$^2$ for 42 days concomitant with focal radiotherapy, preferably 60 Gy administered in 30 fractions of 2 Gy each.

In some embodiments, temozolomide is administered concurrently with RT and azeliragon. In certain embodiments, maintenance TMZ is further administered for a plurality of days following administration of the last dose of RT. In certain embodiments, temozolomide administration is terminated after completion of radiotherapy.

4.2.7. Clinical Benefit

In some embodiments, the treatment is effective to provide a median overall survival of at least 18 months in the GBM population treated according to the methods described herein. In some embodiments, the treatment is effective to provide a median overall survival of at least 24 months, 30 months, 36 months, 42 months, or 48 months in the GBM population treated according to the methods described herein.

In some embodiments, the treatment is effective to provide a 2-year overall survival of at least 30%, 40%, or 50% in the GBM population treated according to the methods described herein. In some embodiments, the treatment is effective to provide a 2-year overall survival of at least 60% in the GBM population treated according to the methods described herein.

4.3. Examples

Below are examples of specific embodiments for carrying out the present invention. The examples are offered for illustrative purposes only, and are not intended to limit the scope of the present invention in any way.

4.3.1. Example 1: Adding Azeliragon Administration to Radiation Therapy (RT) Significantly Improves Survival in Orthotopic Glioblastoma Multiforme (GBM) Tumor Models Standard immunocompetent murine glioblastoma models were used. See, e.g., Oh et al., "Immunocompetent murine models for the study of glioblastoma immunotherapy," *J. Transl. Med.* 12:107 (2014). Murine cell lines GL261 and CT2A were separately implanted into the brain of immune competent C57 albino mice. For each tumor cell line, mice were assigned to one of four treatment groups, with 8 evaluable mice per group (10 mice were injected per group to ensure that at least 8 mice had adequate tumor engraftment): (i) control (tumor implantation without active treatment); (ii) azeliragon; (iii) radiation therapy (RT); and (iv) azeliragon+RT. Azeliragon was administered at a dose of 100 µg/mouse/day by intraperitoneal injection (i.p.).

RT was administered at a dose of 2 Gy for 5 consecutive days. The experimental protocol with treatment timings is schematized in FIG. 1.

FIG. 2 presents Kaplan-Meier survival curves for the GL261 tumor experiment. Azeliragon alone and radiation therapy (RT) alone provided a measurable survival benefit as compared to the control group. The combination of azeliragon and radiation therapy provided significantly longer survival than azeliragon alone or RT alone, with 40% of mice surviving to the prespecified end of study day 60.

FIG. 3 presents Kaplan-Meier survival curves for the CT2A tumor experiment. Azeliragon alone provided no significant benefit, whereas radiation therapy alone increased survival. The combination of azeliragon and RT provided significantly longer survival than azeliragon alone or RT alone.

5. EQUIVALENTS, EMBODIMENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention. It is to be understood that any and all embodiments described herein can be combined with any other embodiment described herein.

All references, issued patents and patent applications cited within the body of the instant specification are hereby incorporated by reference in their entirety, for all purposes.

What is claimed is:

1. A method of treating glioblastoma (GBM), comprising:
   administering a therapeutically effective amount of azeliragon, or a pharmaceutically acceptable salt thereof, and
   co-administering an effective amount of radiation therapy (RT), to a patient who has been diagnosed with glioblastoma.

2. The method of claim 1, wherein cells within the patient's tumor have isocitrate dehydrogenase (IDH) mutations.

3. The method of claim 1, wherein the tumor is IDH-wildtype glioblastoma.

4. The method of claim 1, wherein, in cells within the patient's tumor, the $O^{(6)}$-methylguanine DNA methyltransferase (MGMT) promoter is methylated.

5. The method of claim 1, wherein, in cells within the patient's tumor, the MGMT promoter is unmethylated.

6. The method of claim 1, wherein cells in the patient's tumor have a mutation in at least one gene selected from TP53, EGFR, PTEN, NF1, PIK3CA, PIK3R1, RB1, SPTA1, ATRX, IDH1, KEL, PDGFRA, and GABRA6.

7. The method of claim 1, wherein azeliragon is administered orally.

8. The method of claim 7, wherein azeliragon is administered in a solid oral dosage form.

9. The method of claim 8, wherein the solid dosage form comprises crystalline azeliragon.

10. The method of claim 9, wherein the crystalline azeliragon is Form II.

11. The method of claim 1, wherein azeliragon is administered daily for a plurality of days at an initial loading dose followed thereafter by daily administration for a plurality of days at a maintenance dose.

12. The method of claim 11, wherein the loading dose of azeliragon is administered daily for at least 5 days.

13. The method of claim 11, wherein the loading dose is 60 mg per day.

14. The method of claim 11, wherein the loading dose is 30 mg per day.

15. The method of claim 11, wherein the loading dose is 15 mg per day.

16. The method of claim 11, wherein the maintenance dose is administered daily for at least 6 months.

17. The method of claim 11, wherein the maintenance dose is 20 mg per day.

18. The method of claim 11, wherein the maintenance dose is 10 mg per day.

19. The method of claim 11, wherein the maintenance dose is 5 mg per day.

20. The method of claim 1, wherein the co-administered RT is administered in a plurality of fractionated doses.

21. The method of claim 20, wherein RT is fractionated into 2 Gy daily doses.

22. The method of claim 21, wherein RT is administered at a daily dose of 2 Gy for 5 days a week for 6 weeks, for a total dose of 60 Gy.

23. The method of claim 1, wherein azeliragon is administered daily during co-administration of RT.

24. The method of claim 1, wherein the patient's tumor was surgically resected prior to initiation of azeliragon administration.

25. The method of claim 1, further comprising co-administering temozolomide (TMZ) with the RT.

26. The method of claim 25, wherein TMZ is administered orally at a daily dose of 75 mg/m$^2$.

27. The method of claim 1, wherein the treatment is effective to provide a median overall survival of at least 24 months among treated patients.

28. The method of claim 27, wherein the treatment is effective to provide a median overall survival of at least 30 months among treated patients.

29. The method of claim 1, wherein the treatment is effective to provide a 2-year overall survival of at least 40% among treated patients.

30. The method of claim 29, wherein the treatment is effective to provide a 2-year overall survival of at least 50% among treated patients.

* * * * *